United States Patent
Thaler et al.

(10) Patent No.: US 10,819,168 B2
(45) Date of Patent: Oct. 27, 2020

(54) ELECTRIC MOTOR

(75) Inventors: Wolfgang Thaler, Leutkirch-Herlazhofen (DE); Mark Vohrer, Leutkirch (DE)

(73) Assignee: ATE ANTRIEBSTECHNIK UND ENTWICKLUNGS GMBH, Leutkirch im Allgäu (DE)

( * ) Notice: Subject to any disclaimer, the term of this patent is extended or adjusted under 35 U.S.C. 154(b) by 620 days.

(21) Appl. No.: 13/982,693

(22) PCT Filed: Jan. 30, 2012

(86) PCT No.: PCT/EP2012/000397
§ 371 (c)(1),
(2), (4) Date: Jan. 9, 2014

(87) PCT Pub. No.: WO2012/104055
PCT Pub. Date: Aug. 9, 2012

(65) Prior Publication Data
US 2014/0125180 A1 May 8, 2014

(30) Foreign Application Priority Data
Jan. 31, 2011 (DE) .......... 10 2011 003 400

(51) Int. Cl.
*H02K 1/12* (2006.01)
*H02K 3/24* (2006.01)
(Continued)

(52) U.S. Cl.
CPC .......... *H02K 1/12* (2013.01); *H02K 3/24* (2013.01); *H02K 7/14* (2013.01); *A61B 17/1628* (2013.01);
(Continued)

(58) Field of Classification Search
CPC .......... H02K 1/12; H02K 3/24; H02K 7/14
(Continued)

(56) References Cited

U.S. PATENT DOCUMENTS 4,825,166 A * 4/1989 MacGugan .......... G01R 33/045
29/606
2005/0110354 A1* 5/2005 Datta .......... H02K 1/02
310/88
(Continued)

FOREIGN PATENT DOCUMENTS

| CH | 692 437 A5 | 6/2002 |
| DE | 229929 A1 | 11/1985 |

(Continued)

OTHER PUBLICATIONS

International Search Report for PCT/EP2012/000397 dated Nov. 20, 2012.
(Continued)

*Primary Examiner* — Terrance L Kenerly

(57) ABSTRACT

The invention relates to an electric motor having a rotatably mounted rotor magnet and a stator enclosing the rotor magnet, said stator comprising at least three coil windings and a winding carrier, wherein coil axes of the at least three coil windings are disposed radially to an axis of rotation of the rotor magnet in various radial directions. The coil windings of the electric motor are designed so that a gap that is parallel to the axis of rotation of the rotor magnet extends between at least two adjacent coil windings, in which at least one media line extending in the longitudinal direction is provided.

20 Claims, 2 Drawing Sheets

(51) Int. Cl.
*H02K 7/14* (2006.01)
*H02K 3/44* (2006.01)
*A61B 17/16* (2006.01)
*A61C 1/06* (2006.01)
*H02K 21/02* (2006.01)
*A61B 90/30* (2016.01)

(52) U.S. Cl.
CPC ... *A61B 2090/306* (2016.02); *A61B 2217/005* (2013.01); *A61B 2217/007* (2013.01); *A61C 1/06* (2013.01); *H02K 3/44* (2013.01); *H02K 21/028* (2013.01)

(58) Field of Classification Search
USPC .................................................. 310/156.01
See application file for complete search history.

(56) References Cited

U.S. PATENT DOCUMENTS

| | | | | |
|---|---|---|---|---|
| 2006/0091739 | A1* | 5/2006 | Hilton | H02K 1/04 |
| | | | | 310/45 |
| 2009/0004622 | A1 | 1/2009 | Kuhn et al. | |
| 2009/0160270 | A1 | 6/2009 | Bischof et al. | |
| 2010/0066189 | A1* | 3/2010 | Horng | H02K 1/28 |
| | | | | 310/156.09 |
| 2010/0237732 | A1* | 9/2010 | Grann | F04D 13/027 |
| | | | | 310/103 |
| 2012/0068557 | A1 | 3/2012 | Duesing et al. | |

FOREIGN PATENT DOCUMENTS

| | | |
|---|---|---|
| DE | 69928895 T2 | 7/2006 |
| DE | 10 2005 004 565 A1 | 8/2006 |
| DE | 10 2006 051 510 A1 | 9/2007 |
| EP | 0 854 558 A2 | 7/1998 |
| EP | 1 104 086 A1 | 5/2001 |
| WO | 2010/106157 A2 | 9/2010 |

OTHER PUBLICATIONS

Wikipedia Artikel "Vektorregelung", http://de.wikipedia.org/wiki/Vektorregelung, pp. 1-4.

* cited by examiner

ELECTRIC MOTOR

FIELD OF THE INVENTION

The invention relates to an electric motor according to the preamble of claim 1.

DESCRIPTION OF PRIOR ART

Electric motors of the type mentioned in the beginning are employed, for example, in medical appliances, such as drills, in particular dental drills, cutters, bone cutters, dental mills and saws. In applications of this type, however, various particularities must be observed. Among other things, a compact structure is required, so that the medical instrument comfortably lies in the hand and permits precise and effortless working. At the same time, the motor should be efficient, so that no changes of speed occur under load. It is furthermore necessary for medical instruments to supply the working area with additional media. For example, the working area must be selectively illuminated and cooled or cleaned with water and/or air. These media must be brought to the working area (operation area) through supply lines that are especially provided for this purpose and necessarily must be guided through or past the motor. To ensure the supply with media, it is either necessary to enlarge the diameter of the instrument, making handling more difficult, or the motor must be reduced in size, thus deteriorating the operation behavior and the efficiency of the electric motor.

In the patent application document EP 2073347 A, one tries to at least partially eliminate this conflict between the size and efficiency of the motor by guiding the media lines through a return body of the stator which encapsulates the motor. Since the media lines, however, must have a certain diameter, for example an inner diameter of 1 mm, the return body must necessarily be of a corresponding thickness. Thus, the return body must be thicker than would be required normally. Furthermore, the inhomogeneities then occurring in the return body by the line passages will have an influence on the stator magnetic field, whereby the operation properties may deteriorate.

A different approach is followed in the patent application document EP 0788779 A. EP 0788779 describes a collectorless d. c. motor for driving an engageable dental instrument where the stator air gap winding includes free spaces for the media lines. The free spaces are obtained by arranging a plurality of triangular single coils uniformly and in a partially overlapping manner in the circumferential direction of the stator, so that they form a closed coil ring. By this arrangement of the single coils, on the one hand, a more homogenous magnetic field is formed where cogging torques of the rotor are avoided. On the other hand, the overlapping single coils form a closed coil ring with an irregular outer periphery. These irregularities are formed by the overlapping and form free spaces through which media lines may be guided. Thereby, the return body can be embodied to be symmetrical and thin, and unbalances in the magnetic field guidance are avoided. This can minimize cogging torques of the motor. However, a disadvantage of this arrangement is that by the more homogenous magnetic field, a sensorless detection of the pole position of the magnetic rotor for the speed control of the motor becomes very difficult in particular at low speeds. Furthermore, the free spaces due to the overlapping coils are relatively small, so that the flow rate through the media line is restricted. Another disadvantage of this arrangement is that the coil windings can only be designed as coreless stator air gap windings. This means that due to the overlapping arrangement, the individual coil windings cannot (corelessly) enclose a soft-magnetic core. This deteriorates the efficiency of the motor.

In view of the disadvantages of prior art, the object underlying the invention is to provide a compact electric motor with high efficiency which can be very precisely and exactly controlled down to low speed ranges and which leaves sufficient free spaces for passing through media.

SUMMARY OF THE INVENTION

The object is achieved by an electric motor with a rotatably mounted rotor magnet and a stator enclosing the rotor magnet, said stator comprising at least three coil windings and a winding carrier, wherein coil axes of the at least three coil windings are disposed radially to an axis of rotation of the rotor magnet in various radial directions. The above mentioned object is in particular achieved in that the coil windings are designed so that a gap that is parallel to the axis of rotation extends between at least two adjacent coil windings, so that at least one media line extending in the longitudinal direction can be inserted into the gap. In contrast to the coil arrangement in EP 0788 779, the coils of the present invention are not disposed in an overlapping manner but in such a way that a gap is formed between adjacent coils. The gap can be varied as required by correspondingly designing the windings, depending on the space required for passing through media without changing the diameter of the electric motor. Furthermore, by the gaps between adjacent coils, distinct inhomogeneities of the magnetic flow are formed which can be detected by detecting the mutual induction voltages in the coil windings. The cogging torques caused by the field inhomogeneities may be compensated, even at very low speeds close to 0 revolutions per minute, due to these distinct induction signals by counter control. This means that already when the motor is started, a sufficient signal is available by which the position of the rotor can be detected, so that speed control and a smooth moment of motion are possible within a large speed range, for example 0 to 200,000 revolutions per minute.

For example, a collectorless synchronous motor with a sensorless control can be used. For this, a negative field voltage into the at least one of the at least three coils is used for detecting the rotor position. Sensorless means that no separate sensors are required for detecting the position of the rotor.

In one embodiment, the winding carrier is a cylindrical hollow body, one cylinder wall of the cylindrical hollow body comprising projections in the radial direction towards the cylinder axis corresponding to a number of coil windings which projections are surrounded by the coil windings. The winding carrier preferably contains a soft-magnetic material to increase the inductance of the coils and improve the efficiency of the motor. The projections here serve as mounting and positioning devices of the coil windings. Simultaneously, the projections increase the coil inductances and the force action of the generated magnetic field on the rotor.

The projections may extend from the winding carrier radially outwards or inwards.

If the projections extend radially inwards, an improved force action of the magnetic fields of the individual coil windings on the rotor results because the coil windings are disposed closer to the rotor.

If the projections extend radially outwards, the manufacture of the stator is facilitated because the coil windings may be placed onto the projections of the winding support from outside.

In one embodiment, the winding carrier is made of a stack of stampings. The realization of the winding support with a stack of stampings has the advantage that the complex shape of the winding carrier with the projections can be realized in a simple technical procedure. Moreover, by the use of a stack of stampings, eddy currents in the winding carrier are reduced, in particular if the stampings are mutually insulated. In a particular embodiment, the stampings consist of a nickel steel. Nickel steel on the one hand has a good ferromagnetic (soft-magnetic) characteristic, and on the other hand it is particularly corrosion-resistant. In particular if electric motors are used according to the invention in medical instruments, such as e. g. dental drills, bone cutters, etc., the electric motor must be resistant to corrosive environments because medical instruments are regularly subjected to sterilization processes with aggressive chemicals.

As an alternative, the winding carrier can also be made as a plastic molded part with soft-magnetic material inclusions, for example iron powder. In particular with high piece numbers, manufacturing costs can be reduced thereby. Moreover, with a corresponding design of the mold, edges at the projections of the winding carrier can be avoided, so that damage to the insulation of the winding wires can be avoided. Furthermore, the plastic materials that can be used are nonconductors, so that the formation of eddy currents is minimized. It should be noted, however, that the plastic should have sufficient withstand strength as the high induced voltages occurring in particular at high speeds could cause a breakthrough in the plastic.

In a further alternative, the winding carrier is made of a sintered ceramic part with soft-magnetic material inclusions, such as e. g. iron powder. Winding carriers of ceramic materials have a high mechanical strength, a high electric withstand strength and a high resistance to corrosive materials as they are used, for example, in sterilization processes.

In a particular embodiment, the rotor magnet is a permanent magnet with a tight hermetical casing which is rotationally symmetrically fixed to an axle shaft. High speeds can be achieved due to the symmetric design without strongly loading the bearings due to high unbalances. Furthermore, the hermetically tight casing serves to protect the permanent magnet from corrosion. Since permanent magnets are made of hard-magnetic materials which are highly corrodible, in particular in the application in medical instruments, corrodible components must be protected. In particular, the permanent magnet casing must consist of a material that does not swell nor corrode under the influence of sterilization processes. Since sterilization materials often cause plastic sealing materials to swell and the permanent magnet to quickly corrode, an unprotected or insufficiently protected permanent magnet can, after sterilization processes, quickly lose its operation properties and possibly get locked. For example, the permanent magnet casing can consist of a non-magnetic sleeve of steel, of plastic, such as Teflon, or of a carbon fiber reinforced plastic. As an alternative, the rotor magnet can be a molded part or a sintered part with included magnetic particles, for example magnetized iron powder.

Preferably, the above mentioned embodiments of the electric motor are particularly suited to be used as surgical instrument or as dental instrument, in particular to be used as a drill, a dental drill, a bone cutter or a bone saw.

BRIEF DESCRIPTION OF THE FIGURES

The invention will be described more in detail below with reference to embodiments and to the accompanying drawings, wherein.

DETAILED DESCRIPTION OF EMBODIMENTS

Figure 1:
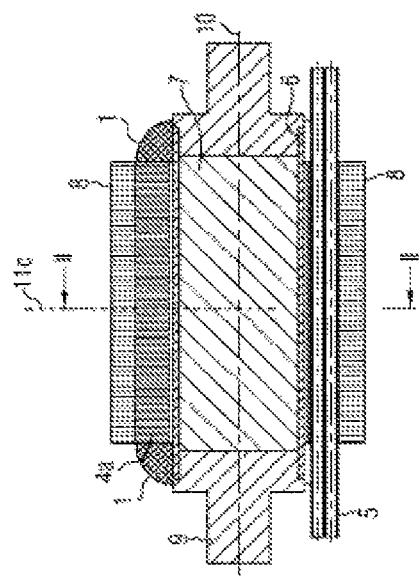
FIG. 1 shows a cross-section of an electric motor according to the present invention.
Figure 2:
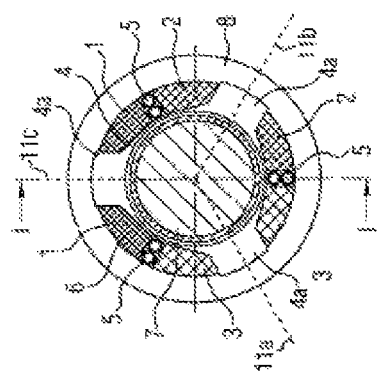
FIG. 2 shows another cross-section of the electric motor according to the present invention.

FIGS. 1 and 2 show cross-sections of an electric motor according to the present invention. FIG. 1 shows a section transverse to the axis of rotation of the rotor, and FIG. 2 shows a cross-section longitudinal to the axis of rotation of the rotor.

In FIG. 1, reference numerals 1, 2 and 3 designate coil windings, reference numeral 4 designates the winding carrier, reference numeral 4a designates a projection of the winding carrier 4, reference numeral 5 designates media lines, reference numeral 6 designates a hermetic casing of a rotor magnet 7, and reference numeral 8 designates a return body. Reference numerals 11a, 11b and 11c designate axes of the coil windings 1, 2 and 3. The coil windings 1, 2 and 3 surround the projections 4a of the winding carrier 4.

When current is supplied to the coil windings 1, 2 and 3, a magnetic field is formed in the projections 4a parallel to the coil axes 11a, 11b and 11c, so that a torque can be applied to the rotor magnet 7 rotatably mounted inside the winding carrier 4.

The coil windings 1, 2 and 3 are made such that there is a gap between adjacent coil windings. Media lines 5 through which water, air and light may be guided may be embedded into this gap. The return body 8 encapsulates the electric motor to the outside. The winding carrier 4, the coils 1, 2 and 3 and the return body 8 form the stator of the electromagnet. The winding carrier 4 and the return body 8 contain soft-magnetic materials to increase the inductances of the coil windings 1, 2 and 3, so that the efficiency of the electric motor is improved. The winding carrier 4 is designed as a cylindrical hollow body. In particular, the hollow space is a circular cylinder in which the cylindrical rotor containing the rotor magnet 7 is rotatably fitted. The inner diameter of the cylindrical hollow body is somewhat larger than the outer diameter of the cylindrical rotor, so that the rotor may rotate relatively to the stator. The cylindrical rotor magnet 7 is hermetically tightly provided with a casing 6 which protects the easily corrosive permanent magnet material from corrosion.

In operation, at least one of the at least three coil windings is supplied with current when the motor is started. The position of the poles of the rotor magnet 7 results from the induction voltage of at least one other one of the at least three coil windings, so that the position of the permanent magnet (rotor magnet 7) relative to the coil windings 1, 2 and 3 can be determined. Then, the coil windings 1, 2 and 3 are supplied with current such that a maximum starting torque is formed. The induced voltages in the coil windings, which are caused by the rotating rotor magnet 7, are constantly monitored, and the current feed to the coil windings 1, 2 and 3 is permanently adjusted until the setpoint speed is reached. When the electric motor is loaded and a change of speed occurs, the change of speed is detected by the monitoring of the mutual induction, and the current feed is adjusted such that the torque is sufficient to achieve the nominal speed. By the distinct unbalance of the magnetic fields of the three coil windings, already very small movements of the rotor magnet 7 can be detected and the control of very low speeds of nearly zero revolutions per minute up to very high speeds, for example approx. 200,000 revolutions per minute, can be realized. To better compensate cogging torques, it is possible to operate the motor with a vector control. For this, all coil windings 1, 2 and 3 are simultaneously fed with current. Depending on the load and speed, the phases and the voltages at the three coil windings are controlled independently and actively corresponding to the rotor position.

FIG. 2 shows a section along line I-I of FIG. 1. FIG. 2 shows the media lines 5 now in a longitudinal section. The stator is formed by the return body 8, the winding carrier 4 with the projections 4*a*, and the coil windings 1, 2 and 3. In FIG. 2, only the coil winding 1 can be seen. The rotor is formed by the rotor magnet 7, the rotor axis 9 and the permanent magnet casing 6 of the rotor magnet 7. The rotor is formed as a circular cylinder, the center of the circle being located on the axis of rotation 10 of the rotor, so that the rotor can rotate about the axis of rotation 10 relatively to the position of the stator. Cutting along the sectional axis II-II, one will obtain again the representation according to FIG. 1.

While the embodiment shown in FIGS. 1 and 2 and in the following FIGS. 3 and 4 include three coils, the present invention is not restricted to three coils, but more than three coils can also be arranged.

In the embodiment according to FIGS. 1 and 2, two media lines each are disposed in the radial direction one behind the other each in a gap between two adjacent coil windings (for example between coil winding 1 and coil winding 2). To ensure the applicability as a dental drill, the outer diameter of the return body 8 should not exceed 2 cm, preferably 1.5 cm to 1.85 cm. The media lines 5 may, in the arrangement shown in FIGS. 1 and 2, then have an outer diameter of 1 mm each. The winding carrier 4 and the return body 8 are made of a soft-magnetic material or a material including soft-magnetic components. For the application as a medical instrument, it should in particular be taken care that the employed materials can be sterilized, i. e. the employed materials must not change their shapes during the sterilization process, for example by swelling, and they must neither change their chemical compositions, for example by oxidizing. In view of fabrication, the use of a stack of stamped nickel steel sheets is advantageous for the winding carrier 4. Nickel steel is a corrosion-resistant ferromagnetic (soft-magnetic) material. Furthermore, the complicated geometry of the winding carrier 4 can be easily achieved by stamping. A design as a stack of stampings also helps to reduce eddy current losses.

For higher piece numbers, a design as an injection-molded part with soft-magnetic inclusions or as a sintered ceramic part with soft-magnetic inclusions can be advantageous from a manufacturing point of view. If plastics are used for injection-molded parts, it should be taken care that the plastic has sufficient withstand strength. For the soft-magnetic inclusions, for example iron powder can be used. As the return body 8, a sleeve can be used which is placed over the winding carrier with the coil windings. Preferably, the return body 8 consists of a soft-magnetic material or a material with soft-magnetic inclusions. For example, a sleeve of nickel steel, an injection-molded sleeve with soft-magnetic inclusions, such as iron powder, or a sintered ceramic sleeve with soft-magnetic inclusions can be used.

Figure 3:
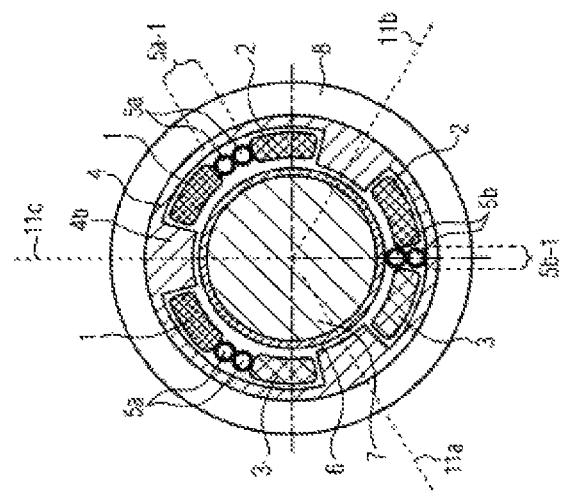
FIG. 3 shows a variant of the embodiment according to FIG. 1.

FIG. 3 shows an embodiment of the electric motor with another arrangement of the media lines. Reference numeral 5*b* shows an arrangement where two media lines are disposed one behind the other in the radial direction. Such an arrangement is also shown in FIG. 1 and FIG. 2. A successive arrangement in the radial direction requires a gap 5*b*-1 between the adjacent coil windings 2 and 3. Reference numeral 5*a* shows an arrangement of two media lines which are arranged one next to the other in a circumferential direction. In this case, a larger diameter of the media lines 5*a* is possible without the complete outer diameter of about 15 to 20 mm having to be enlarged. For example, the outer diameter of the media lines 5*a* may be each 1.5 to 2 mm, compared to the media lines 5*b* arranged one behind the other with an outer diameter of 1 mm each. Here, the media lines 5*a* situated one next the other in the circular direction require a larger gap 5*a*-1 between the adjacent coil windings 1 and 3. The representation shown in FIG. 3 comprises three coil windings 1, 2 and 3 with corresponding three gaps 5*b*-1 and 5*a*-1, where a narrow gap 5*b*-1 and two wide gaps 5*a*-1 are realized. This leads to a further unbalance of the magnetic field, whereby a sensorless detection of the position of the magnetic rotor 7 is possible at even lower speeds.

Although in FIG. 3, an asymmetric arrangement of the media lines with two large gaps 5*a*-1 and one small gap 5*b*-1 is shown, a different asymmetric arrangement with two small gaps 5*b*-1 and one large gap 5*a*-1 is possible. Furthermore, a symmetric arrangement with three wide gaps 5*a*-1 is possible, for example if media lines with an increased diameter are necessary.

The reference numerals in FIG. 3 which are identical to the reference numeral in FIG. 1 here designate each the same technical features, and for illustrating the elements not mentioned with respect to FIG. 3, reference is made to FIG. 1.

Figure 4:
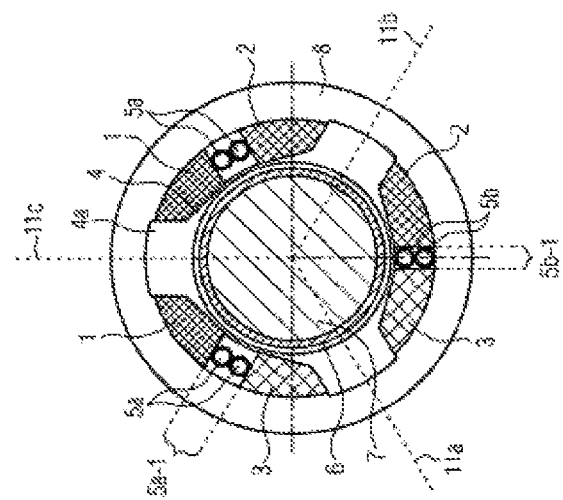
FIG. 4 shows another variant of the embodiment according to FIG. 1.

FIG. 4 shows an alternative embodiment of the electric motor shown in FIG. 1. In FIG. 4, the projections 4*b* of the winding carrier 4 radially project inwards, so that the coil windings 1, 2 and 3 are seated on the projections 4*b* on the inner surface of the winding carrier 4 embodied as cylindrical hollow body. This structural shape has the advantage that the magnetic power transmission from the projections 4*b* to the magnet rotor 7 can be accomplished more directly and power transmission is thus more efficient. FIG. 4 shows again an asymmetric arrangement of the media lines 5*a* and 5*b* as in FIG. 3. As was described in connection with FIG. 3, here, too, any possible combination of radial or circular arrangement of the media lines 5*a* and 5*b* is possible. As in FIG. 3, in FIG. 4, too, reference is made to FIG. 1 for the reference numerals not mentioned here.

An electric motor designed in this way, and as it was described with reference to FIGS. 1 to 4 by way of example, may be advantageously employed for medical instruments, in particular drills, dental drills or bone cutters, as the electric motor can be sterilized and designed for high speed ranges, for example 0-20,000 revolutions/minute, 0-60,000 revolutions/minute, and even 0-200,000 revolutions/minute. Furthermore, the electric motor can be very loadable, that means its speed is very stable under load.

While the present disclosure is described with respect to embodiments as they are illustrated in the above description, the detailed description is not intended to restrict the present disclosure to certain embodiments. The described embodiments are rather intended to only illustrate the various aspects of the present invention by way of example, the scope of the invention being defined by the enclosed claims.

The invention claimed is:

1. An electric motor comprising:
a rotatably mounted rotor magnet; and
a stator enclosing the rotor magnet,
said stator comprising at least three coil windings and a winding carrier, wherein coil axes of the coil windings are disposed radially to an axis of rotation of the rotor magnet in various radial directions,
the coil windings comprising a first coil winding, a second coil winding and a third coil winding,
the winding carrier comprising a first projection, a second projection and a third projection, the first, second and third projections extending radially to the axis of rotation of the rotor magnet in various radial directions,
the first projection and second projection separated by a first circumferential space, the second projection and third projection separated by a second circumferential space, and the third projection and first projection separated by a third circumferential space,
the first circumferential space containing a first part of the first winding and a first part of the second winding,
the second circumferential space containing a second part of the second winding and a first part of the third winding,
the third circumferential space containing a second part of the third winding and a second part of the first winding,
the coil windings being designed such that a gap that is parallel to the axis of rotation extends between at least two of the coil windings, the gap adapted to receive at least one media line extending in a longitudinal direction parallel to the axis of rotation.

2. The electric motor according to claim 1, wherein the electric motor is a collectorless synchronous motor.

3. The electric motor according to claim 1, wherein the projections radially face outwards.

4. The electric motor according to claim 1, wherein the projections radially face inwards.

5. The electric motor according to claim 1, wherein the winding carrier consists of a stack of stampings.

6. The electric motor according to claim 5, wherein the stampings consist of a nickel steel.

7. The electric motor according to claim 1, wherein the winding carrier is a molded plastic part with soft-magnetic material inclusions, or a sintered ceramic part with soft-magnetic material inclusions.

8. The electric motor according to claim 1, wherein the rotor magnet is a permanent magnet which is rotationally symmetrically fixed to an axle shaft.

9. The electric motor according to claim 8, wherein a permanent magnet casing consists of a material which does not swell and does not corrode under the influence of sterilization processes.

10. The electric motor according to claim 9, wherein the permanent magnet casing is a non-magnetic sleeve of steel, plastic or carbon reinforced plastic.

11. The electric motor according to claim 1, wherein the rotor magnet is an injection-molded part or a sintered part with magnetic particles included therein.

12. The electric motor according to claim 11, wherein the magnetic particles are formed of an iron powder.

13. The electric motor according to claim 1, wherein the electric motor is mounted in a surgical instrument or dental instrument.

14. The electric motor according to claim 1, further comprising an equal number of coil windings and projections.

15. The electric motor according to claim 1, wherein the gap is adapted to receive at least two media lines.

16. The electric motor according to claim 1, wherein the gap comprises a first gap between the first part of the first winding and the first part of the second winding.

17. The electric motor according to claim 16, wherein the gap further comprises a second gap between the second part of the second winding and the first part of the third winding.

18. The electric motor according to claim 17, wherein the first gap contains first and second media lines arranged side by side in a circumferential direction with regard to the axis of rotation.

19. The electric motor according to claim 18, wherein the second gap contains third and fourth media lines arranged side by side in a radial direction with regard to the axis of rotation.

20. An electronic motor comprising:
a rotatably mounted rotor magnet; and
a stator enclosing the rotor magnet,
said stator including at least three coil windings and a winding carrier, wherein coil axes of the at least three coil windings are disposed radially to an axis of rotation of the rotor magnet in various radial directions,
the coil windings comprising a first coil winding, a second coil winding and a third coil winding,
the winding carrier comprising a first projection, a second projection and a third projection, the first, second and third projections extending radially to the axis of rotation of the rotor magnet in various radial directions,
the first projection and second projection separated by a first circumferential space, the second projection and third projection separated by a second circumferential space, and the third projection and first projection separated by a third circumferential space,
the first circumferential space containing a first part of the first winding and a first part of the second winding,
the second circumferential space containing a second part of the second winding and a first part of the third winding,
the third circumferential space containing a second part of the third winding and a second part of the first winding,
the first circumferential space including a gap formed parallel to the axis of rotation that extends along side of at least one of the first part of the first winding and the first part of the second winding,
at least one media line extending in the gap in a longitudinal direction parallel to the axis of rotation.

* * * * *